United States Patent [19]
McCarron et al.

[11] Patent Number: 5,911,873
[45] Date of Patent: Jun. 15, 1999

[54] APPARATUS AND METHOD FOR OPERATING AN ISFET AT MULTIPLE DRAIN CURRENTS AND GATE-SOURCE VOLTAGES ALLOWING FOR DIAGNOSTICS AND CONTROL OF ISOPOTENTIAL POINTS

[75] Inventors: Robert Tanner McCarron, Corona del Mar; James R. Gray, Covina, both of Calif.

[73] Assignee: Rosemount Analytical Inc., Irvine, Calif.

[21] Appl. No.: 08/850,602

[22] Filed: May 2, 1997

[51] Int. Cl.[6] .................................................. G01N 27/333
[52] U.S. Cl. ......................... 205/789; 204/401; 204/408; 204/416; 205/787.5; 257/253
[58] Field of Search ................................... 204/401, 416, 204/418, 419, 408; 205/789, 789.5, 787.5; 257/253

[56] References Cited

U.S. PATENT DOCUMENTS

| | | | |
|---|---|---|---|
| 4,020,830 | 5/1977 | Johnson et al. | 128/2 E |
| 4,198,851 | 4/1980 | Janata | 73/23 |
| 4,267,504 | 5/1981 | Bergveld | 324/62 |
| 4,322,680 | 3/1982 | Janata et al. | 324/71 |
| 4,385,274 | 5/1983 | Shimada et al. | 324/71.6 |
| 4,397,714 | 8/1983 | Janata et al. | 204/1 T |
| 4,411,741 | 10/1983 | Janata | 204/1 T |
| 4,456,522 | 6/1984 | Blackburn | 204/416 |
| 4,488,556 | 12/1984 | Ho | 128/635 |
| 4,514,263 | 4/1985 | Janata | 204/1 T |
| 4,532,013 | 7/1985 | Dietz et al. | 204/401 |
| 4,641,084 | 2/1987 | Komatsu | 324/71.5 |
| 4,641,249 | 2/1987 | Gion et al. | 364/496 |
| 4,671,852 | 6/1987 | Pyke | 156/652 |
| 4,691,167 | 9/1987 | Vlekkert et al. | 324/483 |
| 4,701,253 | 10/1987 | Ligtenberg et al. | 204/416 |
| 4,798,655 | 1/1989 | Diamond | 204/1 T |
| 4,879,517 | 11/1989 | Connery et al. | 324/438 |
| 4,952,300 | 8/1990 | Diamond | 204/406 |
| 5,022,980 | 6/1991 | Tanaka et al. | 204/401 |
| 5,319,226 | 6/1994 | Sohn et al. | 257/253 |
| 5,431,883 | 7/1995 | Barraud | 422/82.01 |

OTHER PUBLICATIONS

Karl King, "Dual pH Electrode Improves On–Line Diagnostics", pp. 33–37, 1995 ISA Conference, New Orleans, LA (Oct. 1995).

Prof. Dr. Werner Melzer, "Maintenance Free Online pH–Measurement", pp. 57–64, 1995 ISA Conference, New Orleans, LA (Oct. 1995).

Hon–Sum Wong and Marvin E. White, "A CMOS–Integrated "ISFET–Operational Amplifier" Chemical Sensor Employing Differential Sensing", *IEEE Transactions on Electron Devices*, vol. 36. No. 3, Mar. 1989.

*Primary Examiner*—T. Tung
*Attorney, Agent, or Firm*—Westman, Champlin & Kelly, P.A.

[57] ABSTRACT

An apparatus for measuring ion concentration of a solution includes an ion sensitive field effect transistor (ISFET), a reference device, an ISFET control circuit, a memory, a measurement circuit and a diagnostic circuit. The ISFET has a drain, a source, an ion sensitive gate region and a plurality of device characteristics. The reference device is separated from the gate region by a sample solution. The ISFET control circuit is coupled to the ISFET and operates the ISFET at a drain-source voltage $V_{DS}$ and at n successive drain currents $I_{Di}$ and corresponding gate-source voltages $V_{GSi}$, wherein i is an integer from 1 to n and n is an integer greater than 1. The memory stores the plurality of device characteristics and the n successive drain currents $I_{Di}$ and gate-source voltages $V_{GSi}$. The measurement circuit measures ion concentration of the solution as a function of at least one of the n successive drain currents $I_{Di}$ and gate-source voltages $V_{GSi}$ and the plurality of device characteristics stored in the memory. The diagnostic circuit measures at least one of the device characteristics of the ISFET as a function of the n successive drain currents $I_{Di}$ and gate-source voltages $V_{GSi}$.

20 Claims, 6 Drawing Sheets

APPARATUS AND METHOD FOR OPERATING AN ISFET AT MULTIPLE DRAIN CURRENTS AND GATE-SOURCE VOLTAGES ALLOWING FOR DIAGNOSTICS AND CONTROL OF ISOPOTENTIAL POINTS

BACKGROUND OF THE INVENTION

The present invention relates to an apparatus and method for measuring ion concentration of a solution by operating an ion sensitive field effect transistor (ISFET) at multiple drain currents and gate-source voltages which allows for diagnostics and control of isopotential points.

An ISFET is similar to a metal oxide semiconductor field effect transistor (MOSFET), but does not have a conductive gate terminal. Instead, an ion-sensitive membrane is placed over the gate or channel region and is exposed to a sample solution. The remainder of the ISFET device is encapsulated. The lead that would be attached to the gate terminal of a MOSFET is attached to a reference electrode. The reference electrode is separated from the ion-sensitive membrane by the solution. An ISFET is typically fabricated with other devices, such as temperature transducers, on a common semiconductor chip which is referred to as an ISFET "die". The ISFET die is mounted within a larger sensor support structure and encapsulated with an epoxy, leaving only the ion-sensitive membrane at the gate region exposed to the solution. The ion-sensitive membrane modulates the gate charge, and thus the potential difference between the reference electrode and the source, as a function of the ion concentration in the sample solution. The potential difference between the reference electrode and the source is commonly referred to as the "gate-source" voltage. One or more of the operating characteristics of the ISFET are then measured and used to calculate the ion concentration.

ISFETs are commonly operated in a constant current mode at only one current. A single device can be made to simulate more than one device by operating at more than one current. This makes it possible to carry out some diagnostics and to control the pH of isopotential points.

SUMMARY OF THE INVENTION

The ion concentration measurement apparatus of the present invention includes an ion sensitive field effect transistor (ISFET), a reference device, an ISFET control circuit, a memory, a measurement circuit and a diagnostic circuit. The ISFET has a drain, a source, an ion sensitive gate region and a plurality of device characteristics. The reference device is separated from the gate region by a sample solution. The ISFET control circuit is coupled to the ISFET and operates the ISFET at a drain-source voltage $V_{DS}$ and at n successive drain currents $I_{Di}$ and corresponding gate-source voltages $V_{GSi}$, wherein i is an integer from 1 to n and n is an integer greater than 1. The memory stores the plurality of device characteristics and the n successive drain currents $I_{Di}$ and gate-source voltages $V_{GSi}$. The measurement circuit measures ion concentration of the solution as a function of at least one of the n successive drain currents $I_{Di}$ and gate-source voltages $V_{GSi}$ and the plurality of device characteristics stored in the memory. The diagnostic circuit measures at least one of the device characteristics of the ISFET as a function of the n successive drain currents $I_{Di}$ and gate-source voltages $V_{GSi}$.

In one embodiment, the ISFET control circuit sequentially applies the n successive drain currents $I_{Di}$ as programmed, constant currents. The ion concentration measurement circuit measures the corresponding gate-source voltages $V_{GSi}$ that are required to produce the drain currents $I_{Di}$ and stores the measurements in the memory. In another embodiment, the ISFET control circuit sequentially applies the n successive gate-source voltages $V_{GSi}$ as programmed, constant voltages between the reference device and the source. The ion concentration measurement circuit measures the corresponding drain currents $I_{Di}$ and stores the measurements in the memory.

By operating the ISFET at multiple drain currents and gate-source voltages, more information is gathered regarding the ion concentration measurement than if only a single drain current and gate-source voltage were used. This allows the diagnostic circuit to calculate various ISFET device characteristics or detect changes in their values during operation of the ISFET. These characteristics can then be used to improve the accuracy of the calculations performed by the measurement circuit or predict degradation or failure of the ISFET device while the device is on-line.

DETAILED DESCRIPTION OF THE PREFERRED EMBODIMENTS

Figure 1:
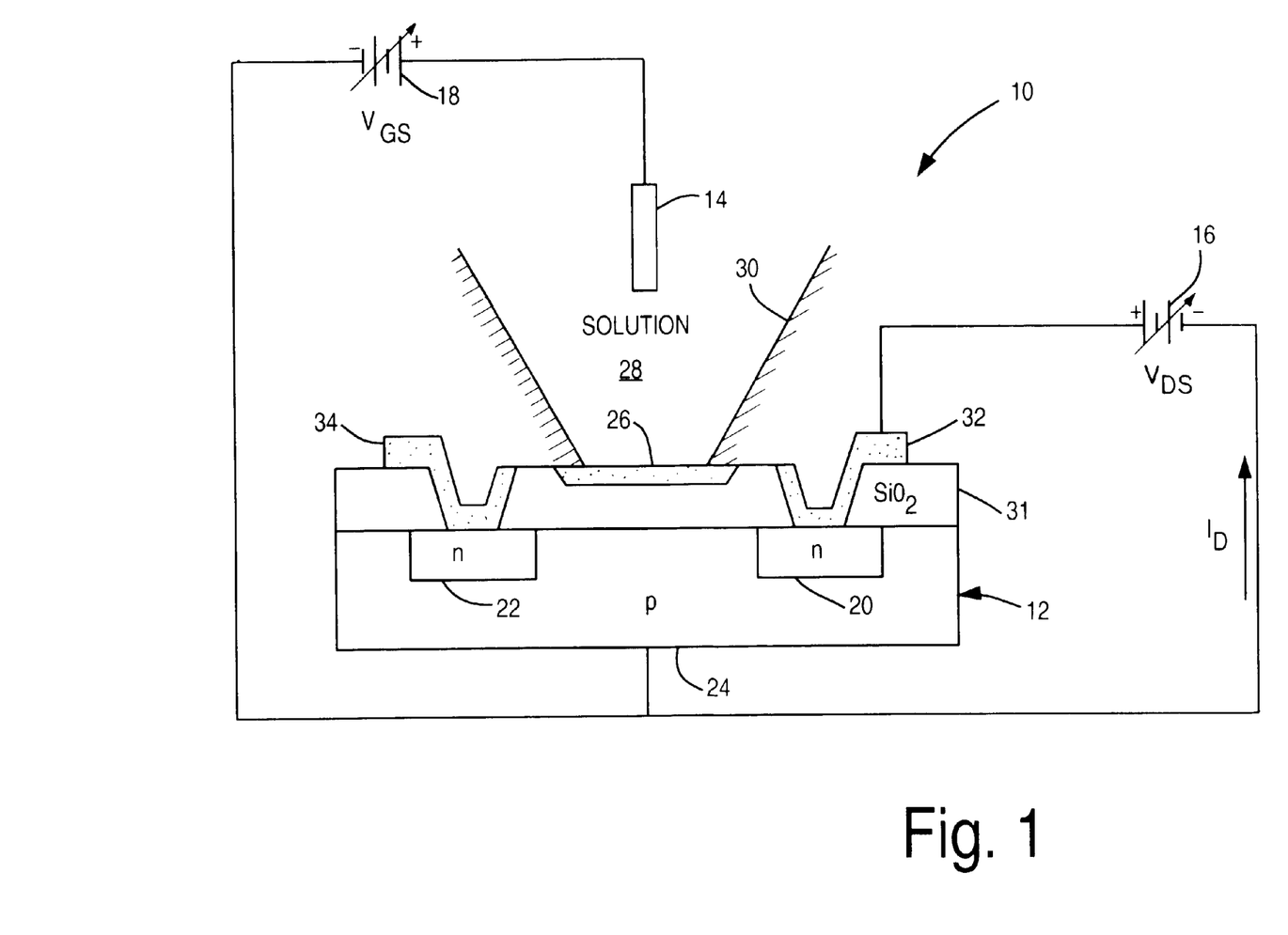
FIG. 1 is a simplified schematic representation of an ion concentration measurement apparatus according to the present invention.

FIG. 1 is a simplified schematic representation of an ion concentration measurement apparatus according to the present invention. Apparatus 10 includes ISFET 12, reference electrode 14, and voltage sources 16 and 18. ISFET 12 includes drain 20, source 22, and substrate 24. Ion sensitive membrane 26 is placed over the gate or channel region of ISFET 12 and is exposed to a sample solution 28. The remainder of the ISFET device is encapsulated with an epoxy 30, for example. Silicon dioxide layer 31 is applied over drain 20, source 22 and substrate 24, except at apertures where metallized contact terminals 32 and 34 are electrically coupled to drain 20 and source 22, respectively. Reference electrode 14 is separated from ion sensitive membrane 26 by solution 28. Voltage source 16 applies a drain-source voltage $V_{DS}$ between drain 20 and source 22. Voltage source 18 applies a gate-source voltage $V_{GS}$ between reference electrode 14 and source 22. Ion sensitive membrane 28 modulates the gate charge, and thus the gate-source voltage $V_{GS}$ as a function of the ion concentration in sample solution 28. A drain current $I_D$, flows through drain 20 as a function of $V_{DS}$ and $V_{GS}$.

In accordance with the present invention, ion concentration measurements are made by operating ISFET 12 in a constant current mode at multiple drain currents, such as four drain currents. ISFET 12 is operated at a first drain current $I_{D1}$ and the gate-source voltage $V_{GS}$ that is required to produce $I_{D1}$ is measured and stored as a first gate-source voltage $V_{GS1}$. Next, ISFET 12 is operated at a second drain current $I_{D2}$ and the gate-source voltage $V_{GS}$ that is required to produce $I_{D2}$ is measured and stored as a second gate-source voltage $V_{GS2}$. This process repeats for a selected number of drain current and gate-source voltage pairs. The drain-source voltage $V_{DS}$ is held constant. The ion concentration is then calculated based on $I_{D1}/V_{GS1}$, $I_{D2}/V_{GS2}$, etc.

In an alternative embodiment, ion concentration measurements are made by operating ISFET 12 in a constant gate-source voltage mode at two or more gate-source voltages. ISFET 12 is operated at a first, constant gate-source voltage $V_{GS}$, and the resulting drain current $I_D$ is measured and stored as a first drain current $I_{D1}$. Next, ISFET 12 is operated at a second, constant gate-source voltage $V_{GS2}$ and the resulting drain current $I_D$ is measured and stored as a second drain current $I_{D2}$. This process repeats for a selected number of drain current and gate-source voltage pairs. The ion concentration is then calculated based on $I_{D1}/V_{GS1}$, $I_{D2}/V_{GS2}$, etc.

Figure 2:
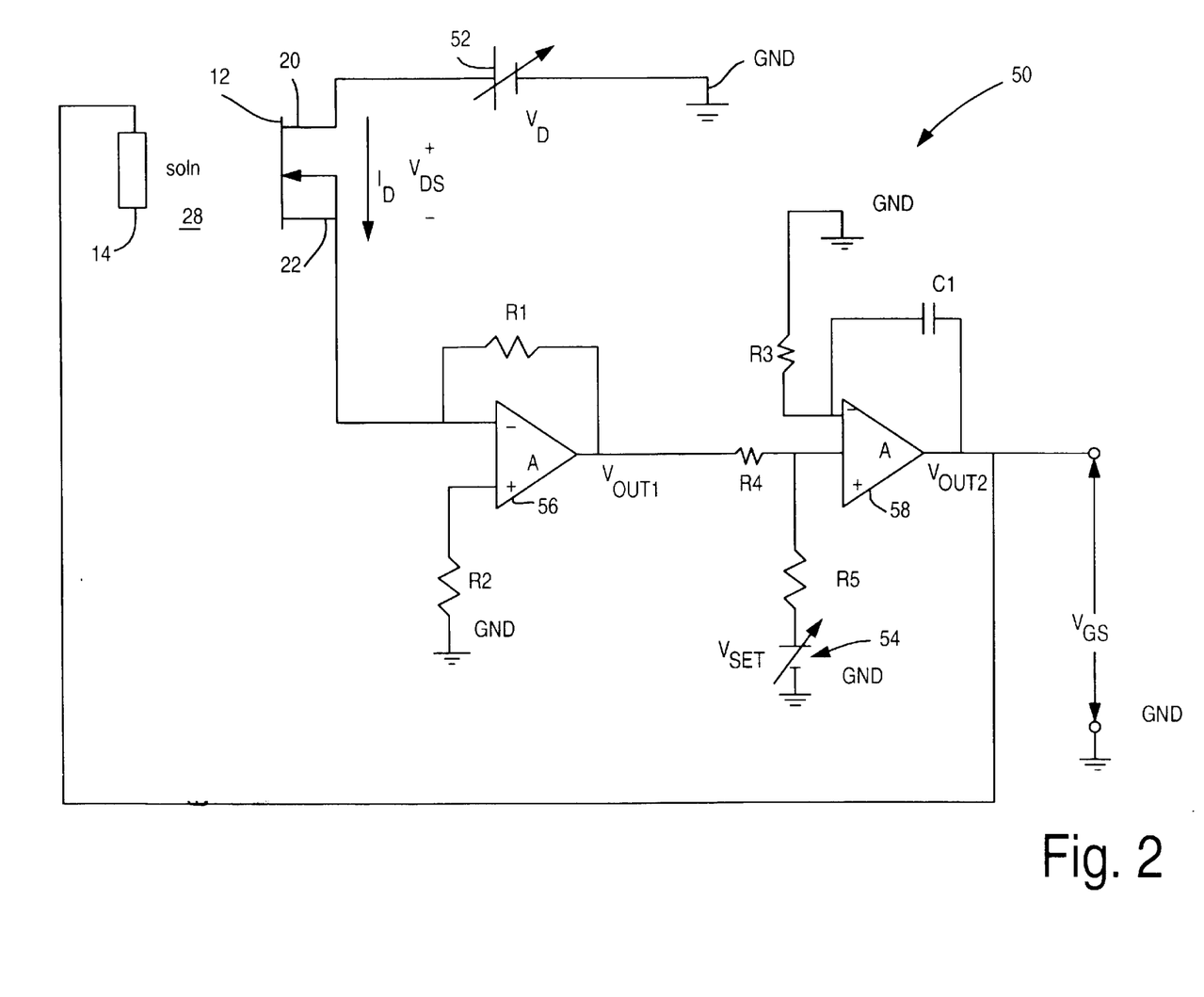
FIG. 2 is a schematic diagram of an ISFET control circuit for operating an ISFET at multiple, constant drain currents.

FIG. 2 is a schematic diagram of an ISFET current control circuit for operating ISFET 12 at multiple, constant drain currents. Current control circuit 50 includes voltage sources 52 and 54, operational amplifiers 56 and 58, resistors R1–R5 and capacitor C1. Voltage source 52 is coupled between drain 20 of ISFET 12 and supply terminal GND. Voltage source 52 applies a constant drain voltage $V_D$, to drain 20. The source 22 of ISFET 12 is coupled to the inverting input of operational amplifier 56. Resistor R2 is coupled between the non-inverting input of operational amplifier 56 and supply terminal GND. Resistor R1 is coupled between the inverting input of operational amplifier 56 and output $V_{OUT1}$.

Resistor R3 is coupled between the inverting input of operational amplifier 58 and supply terminal GND. Resistor R4 is coupled between output $V_{OUT1}$ and the non-inverting input of operational amplifier 58. Resistor R5 and voltage source 54 are coupled together in series between the non-inverting input of operational amplifier 58 and supply terminal GND. Capacitor C1 is coupled between the inverting input of operational amplifier 58 and output $V_{OUT2}$. Output $V_{OUT2}$ of operational amplifier 58 is coupled to reference electrode 14 for supplying the gate-source voltage $V_{GS}$ between reference electrode 14 and supply terminal GND.

During operation, voltage source 52 supplies a constant voltage $V_D$ between drain 20 of ISFET 12 and supply terminal GND. Operational amplifier 56 is essentially a current to voltage converter which adjusts the voltage on output $V_{OUT1}$ as a function of the drain current $I_D$ to maintain its inverting input, and thus source 22 of ISFET 12, at the same voltage as ground terminal GND. Therefore, the drain-source voltage $V_{DS}$ across ISFET 12 is substantially equal to $V_D$ and the voltage at output $V_{OUT1}$ is representative of the drain current $I_D$.

Operational amplifier 58 is essentially an integrator which adjusts the voltage on output $V_{OUT2}$ to maintain the voltage on its non-inverting input substantially the same as the voltage at ground terminal GND. If resistor R4 has the same resistance as resistor R5 and has the same current, $I_D$, then the voltage at output $V_{OUT2}$ is equal and opposite to the offset voltage $V_{SET}$ provided voltage source 54. The output of amplifier 58 is fed back to reference electrode 14 as gate-source voltage $V_{GS}$. Since the voltage at output $V_{OUT1}$ is representative of the drain current $I_D$, the drain current $I_D$ can be set to a predetermined, constant value by selecting the value of $V_{SET}$. The gate-source voltage $V_{GS}$ required to produce the predetermined drain current $I_D$ is measured at output $V_{OUT2}$.

Figure 3:
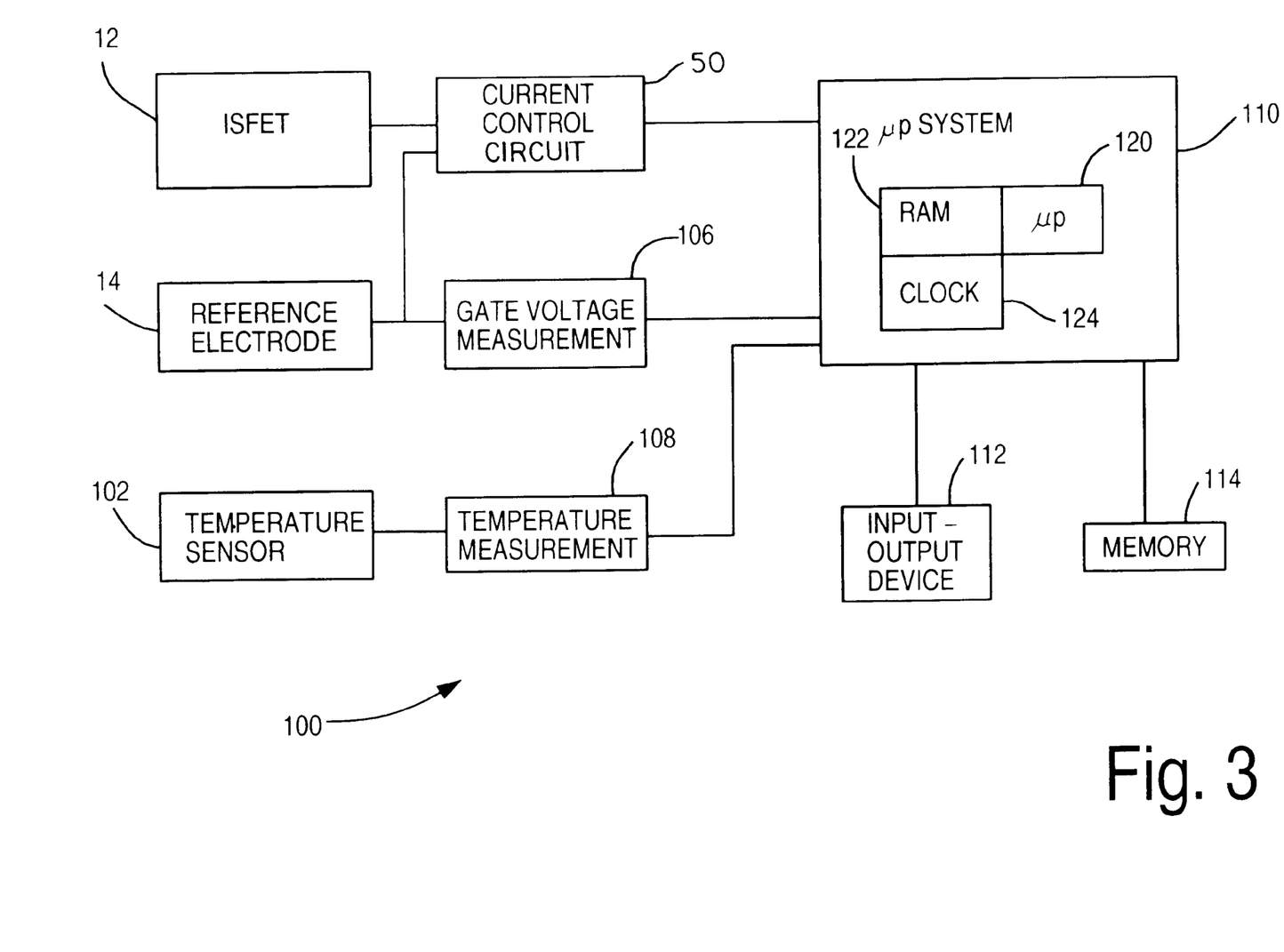
FIG. 3 is a block diagram of a pH measurement instrument in which the ISFET control circuit shown in FIG. 2 is used.

FIG. 3 is a block diagram of a pH measurement instrument in which the ISFET current control circuit shown in FIG. 2 is used. pH measurement instrument 100 includes ISFET 12, reference electrode 14, temperature sensor 102, current control circuit 50, gate voltage measurement circuit 106, temperature measurement circuit 108, microprocessor system 110, input-output device 112 and memory 114. Current control circuit 50 is coupled between ISFET 12, reference electrode 14 and microprocessor system 110 for operating ISFET 12 under the control of microprocessor system 110. Gate voltage measurement circuit 106 is coupled to reference electrode 14 and current control circuit 50 for making measurements of the gate-source voltage $V_{GS}$ (shown in FIG. 2) and for providing an output indicative of the measured voltage to microprocessor system 110. Temperature sensor 102 is in contact with the sample solution and provides and output to temperature measurement circuit 108 indicative of the absolute temperature T of the sample solution. Temperature measurement circuit 108 measures the absolute temperature T and provides an output indicative of the measurement to microprocessor system 110.

Microprocessor system 110 includes microprocessor 120, random access memory (RAM) 122 and clock 124. Microprocessor system 110 executes instructions stored in memory 114 for operating ISFET 12 at selected, predetermined constant drain currents and for making measurements of the corresponding gate-source voltages and temperature. Specifically, microprocessor system 110 controls voltage source 54 to generate different values of the offset voltage $V_{SET}$, which cause predetermined values of the drain current $I_D$ to flow through ISFET 12. With each predetermined drain current, microprocessor system 152 reads the gate-source voltage $V_{GS}$ measured by measurement circuit 106 and stores the measurement in RAM 122 or memory 114. Microprocessor 152 also reads the corresponding temperature measurements made by temperature measurement circuit 108 and stores the value in RAM 122 or memory 114.

Memory 114 also stores the values of the predetermines drain current that correspond to each gate-voltage measurement and the various equations and constants required for making ion concentration measurements, updating and correcting the equation constants and performing various diagnostics, as discussed in more detail below. Memory 114 can include a random access memory, a read only memory or an electrically erasable programmable read-only memory, for example.

The results of the ion concentration measurements and the diagnostics are provided by microprocessor system 110 to input-output device 112. Input-output device 112 can include a display, for example, or can include a transmitter for coupling to a two-wire process control loop which provides an output current to a remote master controller as a function of the measured ion concentration. Such a transmitter can also send and receive digital information superimposed onto the output current which relates to the status of the transmitter, the results of the diagnostics, the measured ion concentration, instructions and calibration information.

Ion concentration measurements are performed by microprocessor system 110 based on equations and ISFET device characteristics that are stored in memory 114. The following equation defines the gate-source voltage $V_{GS}$ as a function of the drain current $I_D$, the pH of the sample solution and the temperature T of the sample solution:

$$V_{GS} = A + \epsilon I_D^{1/2} - (B - HI_D)T + CkTpH, \quad k = \ln(10)R/F \qquad \text{Eq. 1}$$

Equation 1 contains five constants, A, B, C, $\epsilon$ and H. A is in volts and corresponds to terms such as the potential of reference electrode 14, the potential of the solution junction and a contribution from ISFET 12. B is in volts per degree Kelvin and expresses the temperature dependence of reference electrode 14 and the portion of the ISFET temperature dependence which is not also drain current dependent. Ck is in volts per pH unit and includes the efficiency C of ion sensitive membrane 26 and the Nernstian constant k=ln(lO) R/F, which is termed the "slope" of the ISFET. The efficiency C is a dimensionless factor, which is typically on the order of 0.9, and corrects the Nernstian constant k for deviations from ideality. $\epsilon$ is a property of the ISFET device and is a combination of such factors as the charge carrier mobility in the silicon, the geometry of the channel and the capacitance of the insulator area, where the term $\epsilon I_D^{1/2}$ expresses voltage as a function of current. Finally, H is in Ohms per degree Kelvin and expresses the current dependence of the change in gate-source voltage with temperature T. The initial values for A, B, C, $\epsilon$ and H are obtained through factory calibration and are stored in memory 114.

The pH of solution 28 (shown in FIG. 1) is calculated with the equation:

$$\text{pH} = \frac{B - HI_D}{Ck} - \frac{V_{GS} - (A + \epsilon\sqrt{I_D})}{CkT} \quad \text{Eq. 2}$$

where $V_{GS}$ is the measured gate-source voltage on output $V_{OUT2}$ of FIG. 2. Equation 2 can also be written in terms of the pH and the isopotential point at each drain current as:

$$\text{pH} = pH^0 - \frac{V_{GS} - V^0}{CkT} \quad \text{Eq. 3}$$

where, $$pH^0 = \frac{B - HI_D}{Ck} \text{ and } V^0 = A + \epsilon\sqrt{I_D} \quad \text{Eqs. 4 and 5}$$

The pH is calculated at each drain current and the results are averaged.

The isopotential points at the various drain currents can be described by the equation:

$$V_{Ix}^0 = A + \epsilon\left(\frac{B - CkpH_{Ix}^0}{H}\right) \quad \text{Eq. 6}$$

where $pH_{Ix}^o$ is the isopotential pH at drain current $I_x$ and $V_{1x}$ is the gate-source voltage at drain current $I_x$. The drain current required to set an isopotential pH at any pH can be calculated with the equation:

$$I_D = \frac{B - Ck\text{pH}}{H} \quad \text{Eq. 7}$$

This is particularly useful in applications where it is desired to control the process at a single pH. By making the desired pH an isopotential pH, changes in $V_{GS}$ with temperature can be eliminated by operating the ISFET at the drain current determined in Equation 7. This eliminates the need for temperature compensation.

The present pH can also be made an isopotential pH without using the model parameters. If the gate-source voltage is measured at two drain currents at two different temperatures, then the drain current $I^0$ that is required to make the present pH an isopotential pH can be calculated with Equation 8:

$$I^0 = \frac{I_2\left[\frac{V_{GS,ID1,T2} - V_{GS,ID1,T1}}{T_1 - T_2}\right] - I_1\left[\frac{V_{GS,ID2,T2} - V_{GS,ID2,T1}}{T_1 - T_2}\right]}{\left[\frac{V_{GS,ID1,T2} - V_{GS,ID1,T1}}{T_1 - T_2}\right] - \left[\frac{V_{GS,ID2,T2} - V_{GS,ID2,T1}}{T_1 - T_2}\right]}. \quad \text{Eq. 8}$$

Initial Factory Calibration

The initial values for the constants in Equation 1 are determined during factory calibration. In a preferred calibration procedure, ISFET 12 is sequentially placed in three different buffer solutions, I, II and III. Buffer solutions I and II are maintained at a first controlled temperature and buffer solution III is maintained at a second, higher controlled temperature. ISFET 12 is operated at four different drain currents in each buffer solution and the corresponding gate-source voltages are measured.

The coefficients H and $\epsilon$ and the threshold voltage $V_T$ of ISFET 12, are calculated using a second-order regression of Equation 9.

$$V_{GS} = HTI_D + \epsilon\sqrt{I_D} + V_T. \quad \text{Eq. 9}$$

With the measured temperature T and the measured gate-source voltage at a single drain current at two pHs, $pH_1$ and $pH_2$, and at the same temperature, the efficiency parameter C can be calculated with equation 10.

$$C = \frac{V_{GS}(\text{pH}_2) - V_{GS}(\text{pH}_1)}{kT(\text{pH}_2 - \text{pH}_1)}. \quad \text{Eq. 10}$$

With three threshold voltages $V_{Tn}$ at two or three pHs, $pH_n$ and two or three temperatures $T_n$, Equation 11 can be used to calculate the parameters A, B and C.

$$V_{Tn} = A - BT_n + CkT_n pH_n. \quad \text{Eq. 11}$$

Three equations can be solved for the three unknowns. Two of the temperatures can be the same and two of the pHs can be the same.

Diagnostic Measurements

As current control circuit 50 cycles through the various applied currents, microprocessor system 110 receives measurements of the gate-source voltage at each drain current and the temperature. The diagnostics performed by microprocessor system 110 consist largely of using these measured quantities to calculate various ISFET parameters that should remain constant and comparing the calculated values with stored values. If the ISFET parameters vary beyond prescribed limits, microprocessor system 110 notifies the user of a problem through input-output device 112. Most of these diagnostics can be carried out while the sensor is on-line without interrupting the pH measurements.

The diagnostic measurements identify present problems with the operation of ISFET 12 and can be used to predict future problems, such as a failure. For example, one problem may be drift in the reference potential due to dilution of the electrolyte, a decrease in active site density on the ion-selective membrane or a decrease in the capacitance of the oxide layer due to infusion of ions from the sample solution. With the present invention, drift can be identified by observing changes in the parameters of the gate voltage equation, Equation 1.

The output of instrument 100 is pH, which is calculated with Equation 12.

$$\mathrm{pH} = \frac{B - HI_D}{Ck} + \frac{V_{GS} - (A + \varepsilon\sqrt{I_D})}{CkT} \qquad \text{Eq. 12}$$

The parameters A, $\epsilon$, B, H and C are calculated and stored during calibration, which preferably involves at least two buffers at one temperature and one buffer at another temperature. The reliability of the pH calculation depends on the accuracy of the five parameters. With the present invention, the accuracy of these parameters can be verified by obtaining an updated measurement of each parameter, comparing the measurement with the stored value to detect a change and correction of the stored value, if required. The correction would be a substitution of the new, measured value for the old, stored value. A record is kept of the corrections over time so that long-term trends (e.g. reference drift) can be identified.

1. Drain Current Changes; check $\epsilon$ and H

When ISFET 12 is operated at two or more drain currents, the difference between gate-source voltages at the various drain currents should remain constant at a given temperature. Therefore, a change in the following relation indicates a change in $\epsilon$ or H:

$$V_{GS}(I_{D2}) - V_{GS}(I_{D1}) = HT(I_{D2} - I_{D1}) + \varepsilon(\sqrt{I_{D2}} - \sqrt{I_{D1}}) \qquad \text{Eq. 13}$$

2. Drain Current Changes; solve for $\epsilon$, H and $V_T$

Since microprocessor system 110 changes the drain current frequently, as programmed, the parameters $\epsilon$, H and $V_T$ can be calculated at any time. There are three methods for calculating $\epsilon$, H and $V_T$.

In the first method, the temperature and gate-source voltages are measured at four drain current. The parameters $\epsilon$ and H can then be calculated from Equation 14.

$$\frac{V_{GS}(I_{Dn}) - V_{GS}(I_{Dn-1})}{I_{Dn} - I_{Dn-1}} = HT + \frac{\varepsilon}{\sqrt{I_{Dn}} + \sqrt{I_{Dn-1}}}. \qquad \text{Eq. 14}$$

where n is a positive integer ranging from 1 to 4. A plot of $$\frac{V_{GS}(I_{Dn}) - V_{GS}(I_{Dn-1})}{I_{Dn} - I_{Dn-1}}$$

versus $$\frac{1}{\sqrt{I_{Dn}} + \sqrt{I_{Dn-1}}}$$

will give $\epsilon$ as the slope and HT as the intercept.

In the second method, Equation 15 is used to calculate $\epsilon$ and H. This also requires four drain currents.

$$\frac{V_{GS}(I_{Dn}) - V_{GS}(I_{Dn-1})}{\sqrt{I_{Dn}} - \sqrt{I_{Dn-1}}} = HT(\sqrt{I_{Dn}} + \sqrt{I_{Dn-1}}) + \varepsilon. \qquad \text{Eq. 15}$$

A plot of $$\frac{V_{GS}(I_{Dn}) - V_{GS}(I_{Dn-1})}{\sqrt{I_{Dn}} - \sqrt{I_{Dn-1}}}$$

versus $$T(\sqrt{I_{Dn}} + \sqrt{I_{Dn-1}})$$

will give H as the slope and $\epsilon$ as the intercept.

Having calculated $\epsilon$ and H, the threshold voltage $V_T$ can be calculated at any single drain current with Equation 16.

$$V_T = V_{GS} - HTI_D - \varepsilon\sqrt{I_D}. \qquad \text{Eq. 16}$$

In the third method, the temperature and the gate-source voltage at four drain currents are measured, and Equation 17 is be solved for HT, $\epsilon$ and $V_T$.

$$V_{GS} = HTI_D + \varepsilon\sqrt{I_D} + V_T. \qquad \text{Eq. 17}$$

One way to solve Equation 17 is to fit a second order polynomial to a plot of $V_{GS}$ versus $I^{1/2}$ and solve for the coefficients.

3. Temperature Changes, same pH; solve for A

If there is a significant change in temperature during a reasonably short period of time the parameter A can be solved by at least two methods.

In the first method, the gate-source voltage is measured at a single drain current at two temperatures and at the same pH. Equation 18 can then be used to calculate A.

$$V_{GS} = (A + \varepsilon\sqrt{I_D}) - (B - HI_D + Ck\mathrm{pH})T. \qquad \text{Eq. 18}$$

A plot of $V_{GS}$ versus T will have an intercept of $A+\epsilon I_D^{1/2}$. Since $\epsilon I_D^{1/2}$ is known, A is given by the intercept at any drain current $I_D$ minus $\epsilon I_D^{1/2}$.

In the second method, the gate-source voltage is measured at a single drain current at two temperatures and at the same pH. Equation 19 can then be used to calculate A.

$$\frac{V_{GS}}{T} = \frac{(A + \varepsilon\sqrt{I_D})}{T} - (B - HI_D + Ck\mathrm{pH}). \qquad \text{Eq. 19}$$

A plot of $$\frac{V_{GS}}{T}$$

versus $$\frac{1}{T}$$

will have a slope of $A+\epsilon I_D^{1/2}$. Since $\epsilon I_D^{1/2}$ is known, A is given by the slope at any drain current minus $\epsilon I_D^{1/2}$.

4. pH Changes, Same Temperature; solve for C

If there is a significant change in pH during a reasonably short time period a new value for C can be calculated if grab samples are taken at more than one pH. The temperature and gate voltage are measured at a single drain current at two pHs and at a single temperature. The parameter C can then be calculated with Equation 20.

$$C = \frac{V_{GS}(pH_2) - V_{GS}(pH_1)}{kT(pH_2 - pH_1)}.$$  Eq. 20

5. Temperature and pH Changes; solve for A, B and C

If the temperature and the pH change, and if the pH is known in each case by measurement of a grab sample, Equation 21 can be used to calculate A, B and C with three threshold voltages at the different temperatures and pHs.

$$V_{Tn} = A - BT_n + CkT_n pH_n.$$  Eq. 21 where n is a positive integer. Three equations can be solved for three unknowns. Two of the temperatures can be the same and two of the pHs can be the same.

6. No Significant Change in Temperature or pH

If the grab sample pH is different than the pH calculated by the instrument, it is not known whether A, B or C has changed. For a particular sensor in a particular application it may be more likely that A has changed than that B or C have changed, for example. This will have to be determined. If it is assumed that A has changed a correction can be made to A. A new value for A is calculated with Equation 22 using the stored value for C.

$$A_{calc} = A_{store} - CkT(pH_{grab} - pH_{calc}).$$  Eq. 22

This will allow a correct calculation of pH regardless of the actual nature of the change as long as temperature and pH do not change significantly.

If it is more likely that B has changed, a new value for B can be calculated by Equation 23.

$$B_{calc} = B_{store} + CkT(pH_{grab} - pH_{calc})$$  Eq. 23

If it is assumed that C has changed, a new value for C can be calculated by Equation 24.

$$C_{calc} = \frac{pH_{calc}}{pH_{grab}} C_{store}$$  Eq. 24

As an alternative, correction can be equally distributed among A, B and C.

$$pH + \Delta pH = \frac{1}{C + \frac{\Delta C}{3}} \left[ \frac{V_T - \left(A + \frac{\Delta A}{3}\right)}{kT} + \frac{B + \frac{\Delta B}{3}}{k} \right]$$  Eq. 25 where $$\Delta A = A_{calc} - A_{store}$$  Eq. 26

$$\Delta B = B_{calc} - B_{store}$$  Eq. 27

$$\Delta C = C_{calc} - C_{store}$$  Eq. 28

Alternatively, the change can be distributed between any two parameters by using ½ of the delta values for those parameters.

7. With a Significant Temperature Change

After a significant temperature change a new value for A may be calculated. If a grab sample taken soon after the temperature change indicates a change in pH, the new value for A can be preserved and the change in pH can be accommodated by changes in B and C.

$$pH_{grab} = \frac{1}{C + \frac{\Delta C}{2}} \left[ \frac{V_T - (A)}{kT} + \frac{B + \frac{\Delta B}{2}}{k} \right]$$  Eq. 29

Figure 4A:
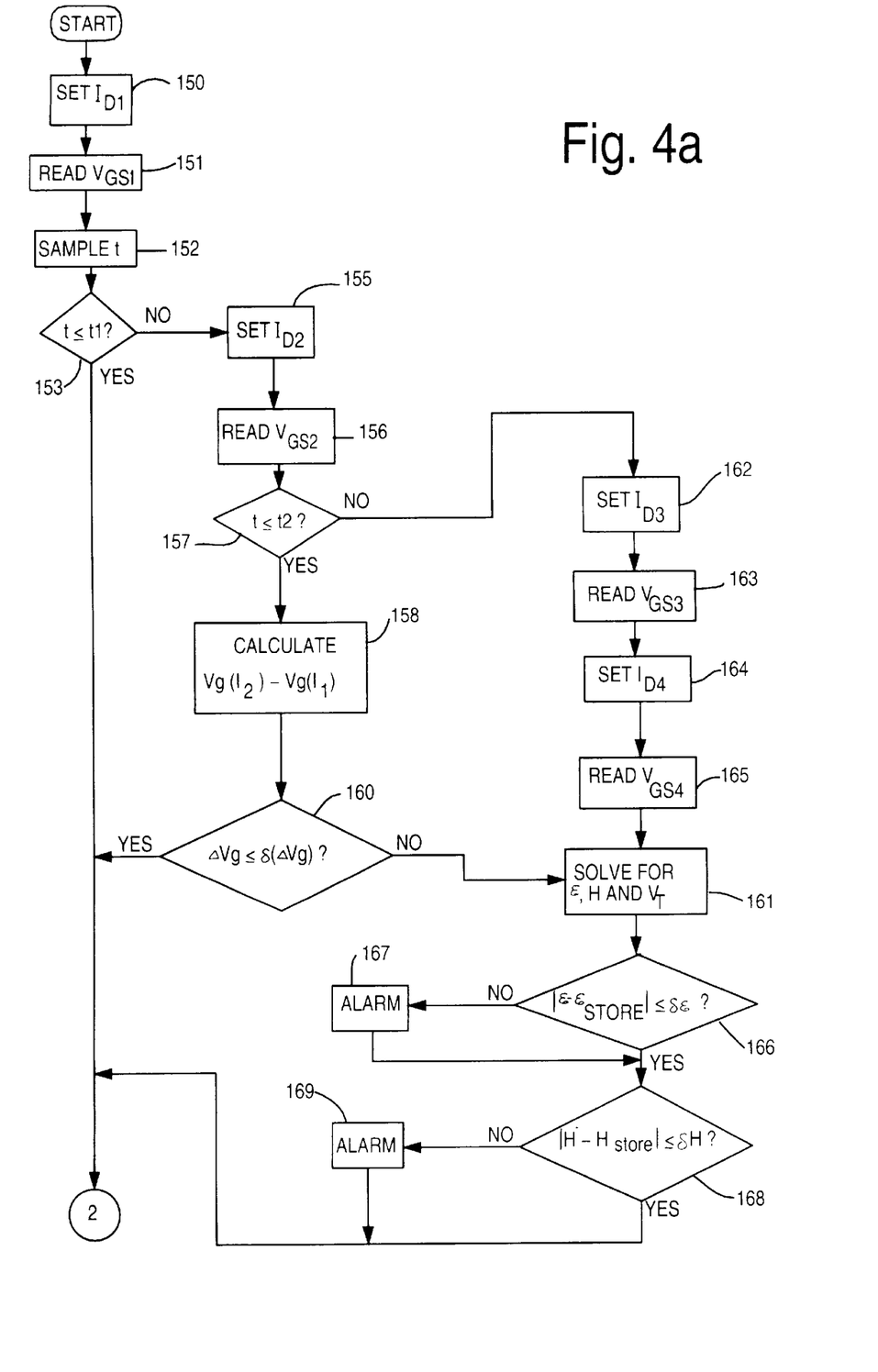
FIGS. 4a and 4b together form a flow chart illustrating the process steps performed when making ion concentration measurements according to the present invention.
Figure 4B:
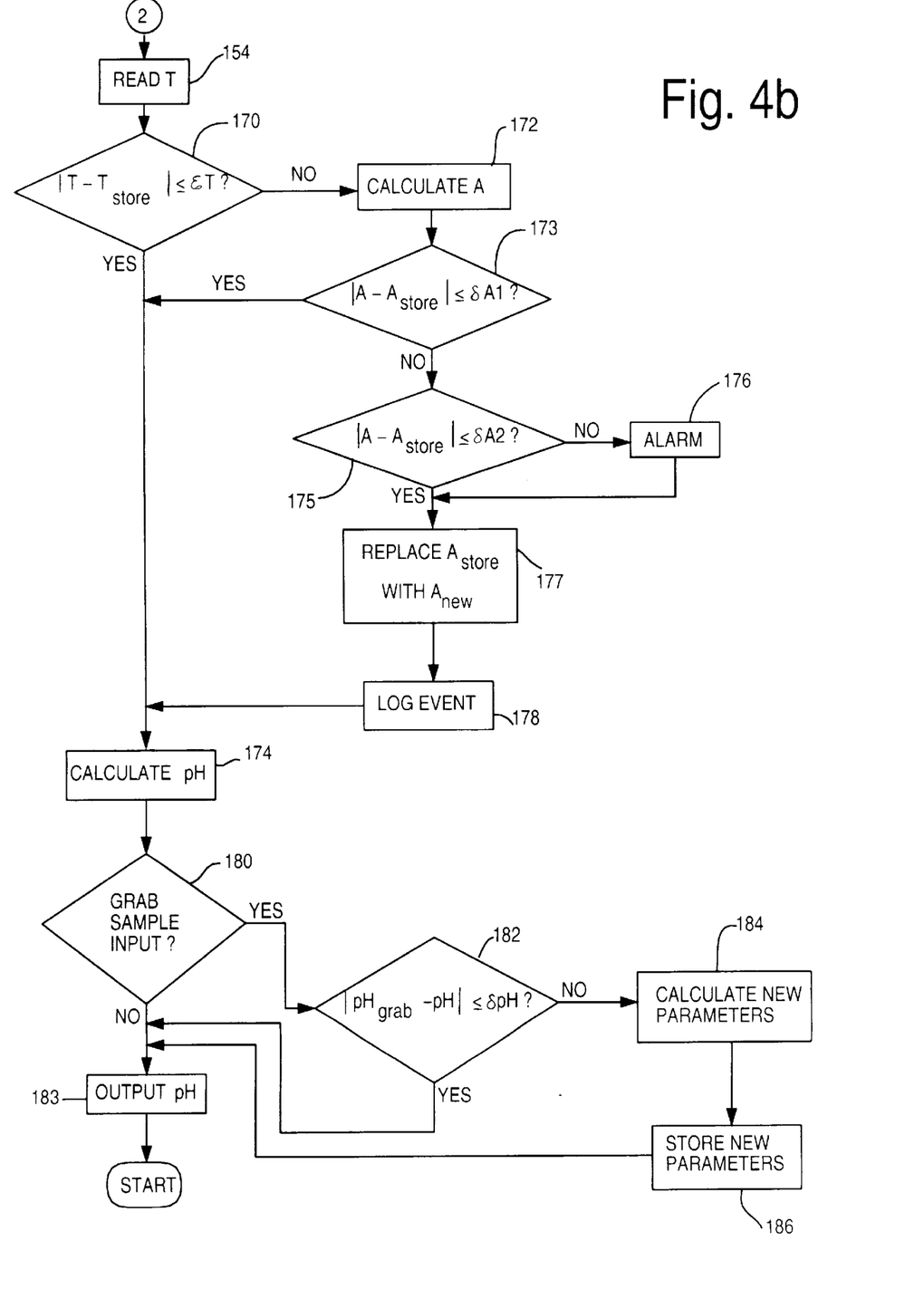

FIGS. 4a and 4b together form a flow chart which illustrates the steps performed by microprocessor system 110 when making ion concentration measurements and diagnostics according to the present invention. At step 150, drain current $I_D$ is set to a first, programmed drain current $I_{D1}$ by adjusting $V_{SET}$ (shown in FIG. 2). The gate-source voltage $V_{GS}$ that is required to produce drain current $I_{D1}$ is measured by gate voltage measurement circuit 106 (shown in FIG. 3) and stored in memory 114 as $V_{GS1}$, at step 151. At step 152, a time t of a timer in microprocessor system 110 is sampled and compared with a first reference time τ1, at step 153. The value of τ1 is selected to adjust how often microprocessor system 110 makes multiple drain current and gate-source voltage measurements. Multiple drain current measurements can be taken every second or at significantly longer time periods, for example. If the sampled time is less than τ1, microprocessor system 110 makes only a single measurement at steps 150 and 151 and then proceeds directly to step 154 (FIG. 4b).

If the sample time t exceeds τ1, then microprocessor system 110 sets the drain current $I_D$ to a second drain current $I_{D2}$, at step 155, and the resulting gate-source voltage $V_{GS}$ is read and stored as $V_{GS2}$. At step 157, the sample time t is compared with a second reference time τ2. If t is less than τ2, then only two drain currents and gate-source voltages will be used, and microprocessor 110 proceeds to step 158. At step 158, the two gate-source voltages $V_{GS1}$ and $V_{GS2}$ are compared according to Equation 13. At step 160, if the change gate-source voltage $\Delta V_{GS}$ is less than a threshold value δ ($\Delta V_{GS}$) then there have been no significant changes in ε, H and $V_T$, and microprocessor system 110 proceeds to step 154 (FIG. 4b). If there has been a significant change, then microprocessor system 110 calculates ε, H and $V_T$ through one of the three methods described with reference to Equations 14–17, at step 161.

Referring back to step 157, if time t is greater than τ2, then microprocessor system 110 reads the gate-source voltages at two additional drain currents $I_{D3}$ and $I_{D4}$, at steps 162–165. Microprocessor 110 then proceeds to step 161, where it calculates ε, H and $V_T$. At step 166, if the difference between the calculated value of ε and the stored, calibration value of ε is greater than a threshold change δε, then microprocessor system 110 issues an alarm at step 167. Microprocessor system 110 also logs the changes in ε and monitors trends in the changes for detecting changes in the system or predicting future failure.

If the change in ε is less than the threshold value, microprocessor system 110 proceeds to step 168 where the calculated value of H is compared with the stored value of H. If the difference is greater than a threshold value δH, then microprocessor system 110 issues an alarm, at step 169. Microprocessor system 110 also logs and monitors the trends in the changes of H.

Microprocessor system 110 then proceeds to step 154 (FIG. 4b), and reads the temperature T of the sample solution through temperature sensor 102 (FIG. 3). The measured temperature T is compared to a stored value Tstore. If the difference exceeds a threshold δT, then there has been a significant change in the temperature of the sample solution and microprocessor system 110 can calculate the parameter A, at step 172, by one of the two methods described with reference to Equations 18 and 19.

At step 173, if the difference between the calculated value of A and the stored value of A is less than a threshold δA1, then the stored value of A is accurate and microprocessor 110 proceeds to step 174. If not, microprocessor system 110 compares the difference to a second threshold δA2, at step 175. If the difference is greater than the second threshold δA2, then there has been a large enough change in A that microprocessor 110 issues an alarm at step 176. If the difference is less than δA2, A is corrected by replacing the stored value of A with the calculated value of A, at step 177. The event is logged at step 178, and microprocessor system 110 proceeds to step 174. By logging the event, microprocessor 110 can maintain a history of the changes in A which can be used to identify present or anticipated problems with the instrument.

At step 174, microprocessor system 110 calculates the pH of the sample solution by one of the methods discussed with reference to Equations 2 and 3. At step 180, if the user has entered a grab sample $pH_{grab}$ through input/output device 112, microprocessor system 110 proceeds to step 182 and compares the difference between the $pH_{grab}$ and the calculated pH. If the difference is less than a threshold δpH, microprocessor system 110 outputs the calculated at pH step 183 and returns to step 150. If the difference is greater than the threshold δpH than microprocessor system 110 calculates new ISFET parameters according to Equations 22–28, at step 184, and stores the new parameters at step 186. It should be understood that the flow chart provided in FIGS. 4a and 4b is an example only and can be modified as desired for various applications.

Constant Gate-Source Voltage, Measured Drain Current Embodiment

Figure 5:
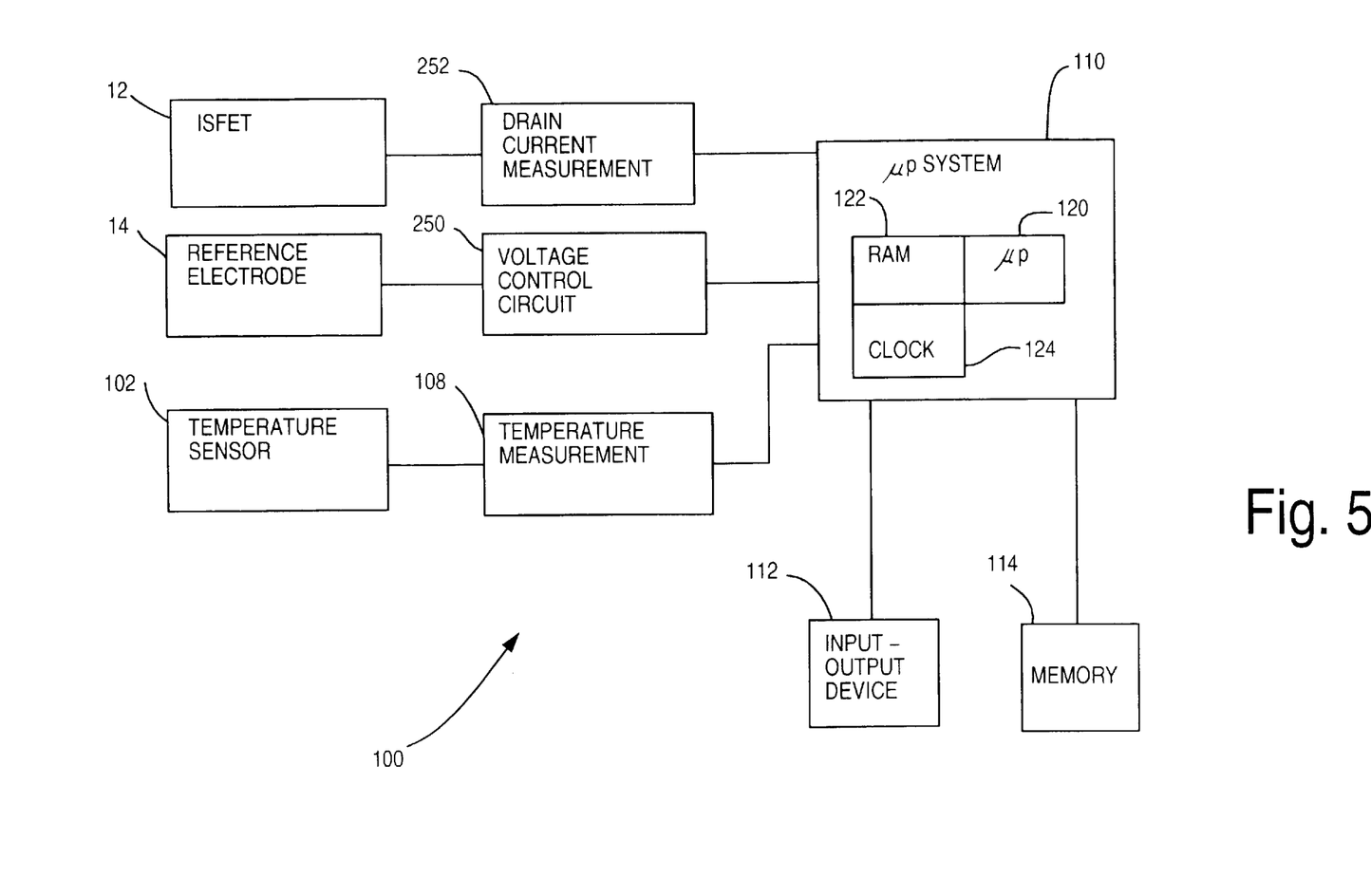
FIG. 5 is a block diagram of a pH measurement instrument for operating an ISFET at multiple, constant gate-source voltages.

In the above examples, ISFET 12 was operated at multiple, constant drain currents and the corresponding gate-source voltages were measured. FIG. 5 is a block diagram of a pH measurement instrument in which ISFET 12 is operated at multiple, constant gate-source voltages and the drain current is measured at each gate-source voltage. The same reference numerals are used in FIG. 5 as were used for FIG. 3 for the same or similar components. Voltage control circuit 250 is coupled between microprocessor system 110 and reference device 114 for sequentially applying different, constant voltages to reference device 14 under the control of microprocessor system 110. Drain current measurement circuit 252 is coupled to ISFET 12 for measuring the corresponding drain currents for each applied gate-source voltage and providing the measurement to microprocessor system 110. Microprocessor system 110 then makes pH calculations based on the gate-source voltages, the measured drain currents and the temperature T.

In this embodiment, Equation 1 can be solved for drain current $I_D$ to arrive at the following ISFET Equation:

$$I_D = \left( \frac{\varepsilon}{2HT} \left( -1 + \sqrt{1 + \frac{4HT}{\varepsilon^2}(V_{GS} - A + BT - CkT\text{pH})} \right) \right)^2 \quad \text{Eq. 30}$$

The isocurrent pH at which the drain current is independent of temperature can be calculated by taking the first derivative of the drain current $I_D$ in Equation 30 with respect to temperature, setting the derivative equal to zero and solving for pH:

$$pH^0 = \frac{B - \frac{H}{\varepsilon^2}(V_{GS} - A)^2}{Ck} \quad \text{Eq. 31}$$

The corresponding isocurrent $I_0$ at a given isocurrent pH can be derived by substituting the results of Equation 31 back into Equation 30:

$$I^0 = \frac{(A - V_{GS})^2}{\varepsilon^2} \quad \text{Eq. 32}$$

These isocurrent points can be used in equations for calculating pH and performing diagnostics as a function of the measured drain current, similar to the equations used with respect to the measured gate-source voltages discussed above.

Conclusion

Previously, there was no information available on the condition of the ISFET device until it was close to catastrophic failure. The accuracy of a pH measurement depends upon how closely the isopotential point, which is used in the calculation of pH, matches the actual isopotential point of the device. There was no method to detect changes in the isopotential point of the ISFET device, except during a laboratory study. The user was totally unaware of this potential cause of a measurement error.

The use of multiple drain current and gate-source voltage measurements allows changes in the isopotential points and the ISFET device characteristics to be detected and measured, which allows correction of the values on-line. For example, a calculation of the standard deviation of the pH values would increase if either or both of the constants H and $\varepsilon$ have changed, which are key indicators of the condition of the ISFET. Significant changes in these constants give an early indication of impending failure. An increase in the standard deviation can be used to trigger an alarm or a recalculation of the constants H and $\varepsilon$ during normal operation of the sensor. The effectiveness of the diagnostics improves as the number of drain current and gate-source voltage measurements increases by allowing statistically significant evaluation of variations, which is the basis for detecting a change.

Although the present invention has been described with reference to preferred embodiments, workers skilled in the art will recognize that changes may be made in form and detail without departing from the spirit and scope of the invention.

What is claimed is:

1. An apparatus for measuring ion concentration of a solution, comprising;
    an ion sensitive field effect transistor (ISFET) having a drain, a source, an ion sensitive gate region and a plurality of device characteristics;
    a reference device separated from the gate region;
    an ISFET control circuit coupled to the ISFET which operates the ISFET at a drain-source voltage $V_{DS}$ and at n successive drain currents $I_{Di}$ and corresponding gate-source voltages $V_{GSi}$ such that the ISFET has an isopotential ion concentration point which is different for each of the n successive drain currents $I_{Di}$ and corresponding gate-source voltages $V_{GSi}$, wherein i is an integer variable from 1 to n and n is an integer greater than 1;

a memory which stores the plurality of device characteristics and the n successive drain currents $I_{Di}$ and gate-source voltages $V_{GSi}$;

measurement means for measuring ion concentration of the solution as a function of at least one of the n successive drain currents $I_{Di}$ and gate-source voltages $V_{GSi}$ and the plurality of device characteristics stored in the memory; and diagnostic means for measuring at least one of the device characteristics of the ISFET as a function of the n successive drain currents $I_{Di}$ and gate-source voltages $V_{GSi}$.

2. The apparatus of claim 1 wherein the diagnostic means calculates a difference between the measured device characteristic and the corresponding device characteristic that is stored in the memory and replaces the corresponding stored device characteristic with the measured device characteristic if the difference exceeds a first threshold value.

3. The apparatus of claim 2 wherein the diagnostic means generates an alarm output if the difference exceeds a second threshold value, which is greater than the first threshold value.

4. The apparatus of claim 1 wherein the diagnostic means stores a history of the measured device characteristic over time within the memory and provides a diagnostic output in response to the stored history.

5. The apparatus of claim 1 wherein the measurement means makes n successive ion concentration measurements of the solution as a function of the stored device characteristics and the n successive drain currents $I_{Di}$ and gate-source voltages $V_{Gsi}$, and provides an ion concentration output based on an average of the n successive ion concentration measurements.

6. The apparatus of claim 1 wherein;

the gate-source voltage $V_{GSi}$ of the ISFET varies with the drain current $I_{Di}$ according to the relation;

$$V_{GSi} = A + \epsilon I_{Di}^{1/2} - (B - H I_{Di})T + CkTpH$$

where T is the temperature of the solution, C is the efficiency of the ion sensitive gate region, k is the slope of the ISFET, pH is the pH of the solution, and A, $\epsilon$, B, H are constants which form the plurality of device characteristics of the ISFET.

7. The apparatus of claim 6 wherein the diagnostic means detects a change in one of $\epsilon$ and H based on the relation:

$$V_{GS2} - V_{GS1} = HT(I_{D2} - I_{D1}) + \epsilon(I_{D2} - I_{D1}^{1/2}).$$

8. The apparatus of claim 6 wherein the ISFET control circuit operates the ISFET at at least four successive drain currents $I_{Di}$ and gate-source voltages $V_{GSi}$ and wherein the diagnostic means calculates e and H as a function of at least the four successive drain currents $I_{Di}$ and gate-source voltages $V_{GSi}$.

9. The apparatus of claim 1 wherein:

the ISFET has an isopotential pH;

the measurement means measures a pH of the solution and comprises means for calculating a target drain current of the ISFET that sets the isopotential pH at the pH of the solution; and the ISFET control circuit comprises means for operating the ISFET at the target drain current.

10. The apparatus of claim 9 wherein the means for calculating calculates the target drain current as a function of the stored device characteristics.

11. The apparatus of claim 9 wherein the solution changes from a first temperature to a second temperature over time and wherein the apparatus further comprises:

a temperature sensor thermally coupled to the solution and having an output representative of the temperature of the solution;

wherein the measurement means comprises means coupled to the output of the temperature sensor for measuring the first and second temperatures;

wherein the ISFET control circuit operates the ISFET at a first gate-source voltage $V_{GS1}$ and a first drain current $I_{D1}$ at the first temperature, and operates the ISFET at a second gate-source voltage $V_{GS2}$ and a second drain current $I_{D2}$ at the second temperature; and wherein the means for calculating calculates the target drain current as a function of $V_{GS1}$, $I_{D1}$, $V_{GS2}$, $I_{D2}$ and the first and second temperatures.

12. The apparatus of claim 1 wherein:

the ISFET control circuit comprises:

means for applying the drain-source voltage $V_{DS}$ across the drain and source;

means for applying the n successive drain currents $I_{Di}$ through the drain sequentially as predetermined, substantially constant currents;

means for applying the n successive gate-source voltages $V_{GSi}$ across the reference device and the source as a function of the corresponding n successive drain currents $I_{Di}$; and means for measuring the n successive gate-source voltages $V_{GSi}$ at the n successive drain currents $I_{Di}$.

13. The apparatus of claim 1 wherein:

the ISFET control circuit comprises:

means for applying the drain-source voltage $V_{DS}$ across the drain and source;

means for applying the n successive gate-source voltages $V_{GSi}$ across the reference device and the source sequentially as predetermined, substantially constant voltages; and means for measuring the n successive drain currents $I_{Di}$ at the n successive gate-source voltages $V_{GSi}$.

14. The apparatus of claim 1 and further comprising a temperature sensor electrically coupled to the measurement means, which measures an absolute temperature T of the solution and wherein:

n is at least three;

the ISFET has a minimum gate-source threshold voltage $V_T$ and a current dependence, H, of the change in the gate-source voltage $V_{GSi}$ with the absolute temperature T of the ISFET; and the diagnostic means comprises means for calculating H and $\epsilon$ of the ISFET and the minimum gate-source threshold voltage $V_T$ of the ISFET during operation of the ISFET based on a second order regression of the relation:

$$V_{GSi} = HT\,I_{DSi} + \epsilon\sqrt{I_{DSi}} + V_T$$

where $\epsilon$ is a constant.

15. An apparatus for measuring ion concentration of a solution, comprising:

an ion sensitive field effect transistor (ISFET) having a drain, a source and an ion sensitive gate region;

a reference device separated from the gate region;

an ISFET control circuit coupled to the ISFET for applying a drain-source voltage $V_{DS}$ across the drain and source and for operating the ISFET at n successive drain currents $I_{Di}$ and corresponding gate-source voltages $V_{GSi}$, wherein i is an integer variable from 1 to n and n is an integer greater than 1, wherein the drain currents flow through the drain of the ISFET and the gate-source voltages are referenced between the reference device and the source, and wherein the ISFET has an iso potential ion concentration point which is different for each of the n successive drain currents $I_{Di}$ and corresponding gate-source voltages $V_{GSi}$;

a memory which stores the n successive drain currents $I_{Di}$ and gate-source voltages $V_{GSi}$; and measurement means for making n successive ion concentration measurements of the solution as a function the n successive drain currents $I_{Di}$ and gate-source voltages $V_{GSi}$ and for providing an ion concentration output based on an average of the n successive ion concentration measurements.

16. A method of measuring ion concentration of a solution with an apparatus comprising a reference device and an ion sensitive field effect transistor (ISFET) having a drain, a source, an ion sensitive gate region and a plurality of device characteristics, wherein the ion sensitive gate region and the reference device are exposed to and separated by the solution, the method comprising:

applying a drain-source voltage $V_{DS}$ across the drain and source;

operating the ISFET at n successive drain currents $I_{Di}$ and corresponding gate-source voltages $V_{GSi}$ such that the ISFET has an isopotential ion concentration point which is different for each of the n successive drain currents $I_{Di}$ and corresponding gate-source voltages $V_{GSi}$, wherein i is an integer variable from 1 to n and n is an integer greater than 1, and wherein the drain currents flow through the drain of the ISFET and the gate-source voltages are referenced between the reference device and the source;

storing the plurality of device characteristics and the n successive drain currents $I_{Di}$ and gate-source voltages $V_{GSi}$;

measuring ion concentration of the solution as a function of at least one of the n successive drain currents $I_{Di}$ and gate-source voltages $V_{GSi}$ and the stored device characteristics; and measuring at least one of the device characteristics of the ISFET as a function of the n successive drain currents $I_{Di}$ and gate-source voltages $V_{GSi}$.

17. The method of claim 16 and further comprising:

calculating a difference between the measured device characteristic and the corresponding stored device characteristic; and replacing the corresponding stored device characteristic with the measured device characteristic if the difference exceeds a first threshold value.

18. The method of claim 17 and further comprising generating an alarm output if the difference exceeds a second threshold value, which is greater than the first threshold value.

19. The method of claim 16 and further comprising:

storing a history of the measured device characteristic over time; and providing a diagnostic output in response to the stored history.

20. The method of claim 16 and further comprising:

making n successive ion concentration measurements as a function of the stored device characteristics and the n successive drain currents $I_{Di}$ and gate-source voltages $V_{GSi}$; and providing an ion concentration output based on an average of the n successive ion concentration measurements.

* * * * *

UNITED STATES PATENT AND TRADEMARK OFFICE
CERTIFICATE OF CORRECTION

PATENT NO.   : 5,911,873
DATED        : June 15, 1999
INVENTOR(S)  : Robert T. McCarron et al.

It is certified that error appears in the above-identified patent and that said Letters Patent is hereby corrected as shown below:

Col. 13, line 57 change "e" to --$\epsilon$--.

Signed and Sealed this

Eighteenth Day of January, 2000

Attest:

Q. TODD DICKINSON

Attesting Officer

Commissioner of Patents and Trademarks